United States Patent
Rao et al.

(10) Patent No.: US 6,551,843 B1
(45) Date of Patent: Apr. 22, 2003

(54) METHODS FOR ENHANCING BINDING INTERACTIONS BETWEEN MEMBERS OF SPECIFIC BINDING PAIRS

(75) Inventors: Galla Chandra Rao, Princeton, NJ (US); Leon Terstappen, Huntingdon Valley, PA (US); Paul Liberti, Hundingdon Valley, PA (US)

(73) Assignee: Immunivest Corporation, Wilmington, DE (US)

( * ) Notice: Subject to any disclaimer, the term of this patent is extended or adjusted under 35 U.S.C. 154(b) by 0 days.

(21) Appl. No.: 09/240,939

(22) Filed: Jan. 29, 1999

(51) Int. Cl.⁷ .................. G01N 33/53; G01N 33/553
(52) U.S. Cl. .................. 436/526; 435/7.1; 435/7.5; 435/7.9; 435/7.92
(58) Field of Search .................. 435/7.1, 7.5, 7.9, 435/7.92; 436/526

(56) References Cited

U.S. PATENT DOCUMENTS

| | | |
|---|---|---|
| 3,970,518 A | 7/1976 | Giaever |
| 4,018,886 A | 4/1977 | Giaever |
| 4,267,234 A | 5/1981 | Rembaum |
| 4,375,407 A | 3/1983 | Kronick |
| 4,554,088 A | 11/1985 | Whitehead et al. |
| 4,795,698 A | 1/1989 | Owen et al. |
| 5,186,827 A | 2/1993 | Liberti et al. |
| 5,215,926 A | 6/1993 | Etchells, III et al. |
| 6,033,574 A | 3/2000 | Siddiqi |
| 6,228,268 B1 | 5/2001 | Siddiqi |
| 6,231,760 B1 | 5/2001 | Siddiqi |

FOREIGN PATENT DOCUMENTS

| | | | |
|---|---|---|---|
| EP | 0 295 965 | * | 12/1988 |
| WO | 96/07101 | * | 3/1996 |
| WO | WO 96/26011 | | 8/1996 |
| WO | WO 97/46882 | * | 12/1997 |

* cited by examiner

*Primary Examiner*—Brenda Brumback
(74) *Attorney, Agent, or Firm*—Dann, Dorfman, Herrell and Skillman (57) ABSTRACT

Disclosed is a method that improves the efficiency of reactions between specific binding pairs. By translating one member of the pair through a suspension of the second member, or across a surface to which the second member is immobilized, collision and binding frequencies are greatly increased. The resulting increased binding frequency allows for reduced incubation times and lower incubation temperatures. The enhanced collisions are advantageous for both molecular reactions, in which mixing is not always effective, and cellular reactions, in which the cells may be damaged by mixing.

8 Claims, 7 Drawing Sheets

METHODS FOR ENHANCING BINDING INTERACTIONS BETWEEN MEMBERS OF SPECIFIC BINDING PAIRS

FIELD OF THE INVENTION

This invention relates to the fields of specific binding pair interactions, bioentity separations and the isolation of rare substances from biological fluids. Methods are provided for enhancing such bioseparations, preferably via enhanced magnetic loading onto target entities, thereby facilitating biochemical and diagnostic analysis of target entities so isolated.

BACKGROUND OF THE INVENTION

There are a substantial number of manufacturing, analytical and laboratory processes and procedures which involve specific binding pair interactions. Many laboratory and clinical procedures are based on such interactions, referred to as bio-specific affinity reactions. Such reactions are commonly utilized in diagnostic testing of biological samples, or for the separation of a wide range of target substances, especially biological entities such as cells, viruses, proteins, nucleic acids and the like. It is important in practice to perform the specific binding pair interactions as quickly and efficiently as possible. These reactions depend on classical chemical considerations such as temperature, concentration and affinity of specific binding pair members for one another. In the ideal, separations employing specific binding partners which rapidly form multiple non-covalent bonds are utilized. The use of such binding partners is important, particularly when the concentration of one of the specific binding pair members to be isolated is extremely low, as often is the case in biological systems. Of course, concentration considerations are relevant in other separation processes, such as in water purification, or in applications where it is necessary to remove trace contaminants or other undesirable products.

Various methods are available for binding, separating or analyzing the target substances mentioned above based upon complex formation between the substance of interest and another substance to which the target substance specifically binds. Separation of the resulting complexes from solution or from unbound material may be accomplished gravitationally, e.g. by settling, or, alternatively, by centrifugation of finely divided particles or beads coupled to the ligand substance. If desired, such particles or beads may be made magnetic to facilitate the bound/free separation step. Magnetic particles are well known in the art, as is their use in immune and other bio-specific affinity reactions. See, for example, U.S. Pat. No. 4,554,088 and Immunoassays for Clinical Chemistry, pp. 147–162, Hunter et al. eds., Churchill Livingston, Edinborough (1983). Generally, any material which facilitates magnetic or gravitational separation, may be employed for this purpose. However, processes relying on magnetic principles are preferred.

Magnetic particles generally fall into two broad categories. The first category includes particles that are permanently magnetizable, or ferromagnetic; and the second comprises particles that demonstrate bulk magnetic behavior only when subjected to a magnetic field. The latter are referred to as magnetically responsive particles. Materials displaying magnetically responsive behavior are sometimes described as superparamagnetic. However, materials exhibiting bulk ferromagnetic properties, e.g., magnetic iron oxide, may be characterized as superparamagnetic when provided in crystals of about 30 nm or less in diameter. Larger crystals of ferromagnetic materials, by contrast, retain permanent magnet characteristics after exposure to a magnetic field and tend to aggregate thereafter due to strong particle-particle interaction.

Magnetic particles can be classified as large (1.5 to about 50 microns), small (0.7–1.5 microns), and colloidal or nanoparticles (<200 nm). The latter are also called ferrofluids or ferrofluid-like particles and have many of the properties of classical ferrofluids. Liberti et al pp 777–790, E. Pelezzetti (ed) "Fine Particle Science and Technology, Kluver Acad. Publishers, Netherlands, Small magnetic particles are quite useful in analyses involving bio-specific affinity reactions, as they are conveniently coated with biofunctional polymers (e.g., proteins), provide very high surface areas and give reasonable reaction kinetics. Magnetic particles ranging from 0.7–1.5 microns have been described in the patent literature, including, by way of example, U.S. Pat. Nos. 3,970,518; 4,018,886; 4,230,685; 4,267,234; 4,452,773; 4,554,088; and 4,659,678. Certain of these particles are disclosed to be useful solid supports for immunologic reagents.

In addition to the small magnetic particles mentioned above, there is a class of large magnetic particles (>1.5 microns to about 50 microns) which also have superparamagnetic behavior. Such materials include those invented by Ugelstad (U.S. Pat. No. 4,654,267) and manufactured by Dynal, (Oslo, Norway). Polymer particles are synthesized, and through a process of particle swelling, magnetite crystals are embedded therein. Other materials in the same size range are prepared by performing the synthesis of the particle in the presence of dispersed magnetite crystals. This results in the trapping of magnetite crystals thus making the materials magnetic. In both cases, the resultant particles have superparamagnetic behavior, readily dispersing upon removal of the magnetic field. Unlike magnetic colloids or nanoparticles referred to above, such materials, as well as small magnetic particles, because of the mass of magnetic material per particle are readily separated with simple laboratory magnetics. Thus, separations are effected in gradients as low as a few hundred gauss/cm, to up to about 1.5 kilogauss/cm. Colloidal magnetic particles (below approximately 200 nm) require substantially higher magnetic gradients for separation because of their diffusion energy, small magnetic mass/particle and stokes drag.

U.S. Pat. No. 4,795,698 to Owen et al. relates to polymer-coated, sub-micron size colloidal superparamagnetic particles. The '698 patent describes the manufacture of such particles by precipitation of a magnetic species in the presence of a biofunctional polymer. The structure of the resulting particles, referred to herein as single-shot particles, has been found to be a micro-agglomerate in which one or more ferromagnetic crystallites having a diameter of 5–10 nm are embedded within a polymer body having a diameter on the order of 50 nm. These particles exhibit an appreciable tendency not to separate from aqueous suspensions for observation periods as long as several months. Molday (U.S. Pat. No. 4,452,773) describe a material which is similar in properties to those described in the '698 patent of Owen et al. produced by forming magnetite and other iron oxides from $Fe^{+2}/Fe^{+3}$ via base addition in the presence of very high concentrations of dextran. Materials so produced have colloidal properties. This process has been commercialized by Miltenyi Biotec, (Bergisch Gladbach, Germany). Those products have proved to be very useful in cell separation assays.

Another method for producing superparamagnetic colloidal particles is described in U.S. Pat. No. 5,597,531. In contrast to the particles described in the '698 patent, these latter particles are produced by directly coating a biofunctional polymer onto pre-formed superparamagnetic crystals which have been dispersed by sonic energy into quasi-stable crystalline clusters ranging from about 25 to 120 nm. The resulting particles, referred to herein as direct-coated or DC particles, exhibit a significantly larger magnetic moment than the nanoparticles of Owen et al. or Molday et al. having the same overall size.

Magnetic separation techniques utilize magnetic field generating aparatus to separate ferromagnetic bodies from the fluid medium. In contrast, the tendency of colloidal superparamagnetic particles to remain in suspension, in conjunction with their relatively weak magnetic responsiveness, requires the use of high-gradient magnetic separation (HGMS) techniques in order to separate such particles from a fluid medium in which they are suspended. In HGMS systems, the gradient of the magnetic field, i.e., the spatial derivative, exerts a greater influence upon the behavior of the suspended particles than is exerted by the strength of the field at a given point.

High gradient. magnetic separation is useful for separating a wide variety of biological materials, including eukaryotic and prokaryotic cells, viruses, nucleic acids, proteins, and carbohydrates. in methods known heretofore, biological material has been separable by means of HGMS if it possesses at least one characteristic determinant capable of being specifically recognized by and bound to a binding agent, such as an antibody, antibody fragment, specific binding protein (e.g., protein A, streptavidin), lectin, and the like.

HGMS systems can be divided into two broad categories. One such category includes magnetic separation systems that employ a magnetic circuit that is situated externally to a separation chamber or vessel. Examples of such external separators (or open field gradient separators) are described in U.S. Pat. No. 5,186,827. In several of the embodiments described in the '827 patent, the requisite magnetic field gradient is produced by positioning permanent magnets around the periphery of a non-magnetic container such that the like poles of the magnets are in a field-opposing configuration. The extent of the magnetic field gradient within the test medium that may be obtained in such a system is limited by the strength of the magnets and the separation distance between the magnets. Hence, there is a finite limit to gradients that can be obtained with external gradient systems. In copending U.S. Provisional Application No. 60/098,021, means for maximizing radial gradients and methods for maximizing separation efficiency via a novel vessel design are disclosed. Such vessels can be used for practicing the methods described herein.

Another type of HGMS separator utilizes a ferromagnetic collection structure that is disposed within the test medium in order to 1) intensify an applied magnetic field and 2) produce a magnetic field gradient within the test medium. In one known type of internal HGMS system, fine steel wool or gauze is packed within a column that is situated adjacent to a magnet. The applied magnetic field is concentrated in the vicinity of the steel wires so that suspended magnetic particles will be attracted toward, and adhere to, the surfaces of the wires. The gradient produced on such wires is inversely proportional to the wire diameter whereas magnetic "reach" decreases with diameter. Hence, very high gradients can be generated.

One drawback of internal gradient systems is that the use of steel wool, gauze material, or steel microbeads, may entrap non-magnetic components of the test medium by capillary action in the vicinity of intersecting wires or within interstices between intersecting wires. Various coating procedures have been applied to such internal gradient columns (U.S. Pat. Nos. 4,375,407 & 5,693,539), however, the large surface area in such systems still creates recovery issues via adsorption. Hence, internal gradient systems are not desirable, particularly when recovery of very low frequency captured entities is the goal of the separation. Further, they make automation difficult and costly.

On the other hand, cell separations using HGMS based approaches with external gradients provide a number of conveniences. First, simple laboratory tubes such as test tubes, centrifuge tubes, or even Vacutainers (used for blood collection) may be employed. When external gradients are of the kind where separated cells are effectively monolayered, as is the case with quadrupole/hexapole devices as described in U.S. Pat. No. 5,186,827 or the opposing dipole arrangement described in U.S. Pat. No. 5,466,574, washing of cells and subsequent manipulations are facilitated. Furthermore, recovery of the cells from tubes or similar containers is a simple and efficient process. This is particularly the case when compared to recoveries from high gradient columns. Such separation vessels also provide another important feature which is the ability to reduce volume of the original sample. For example, if a particular human blood cell subset, (e.g. magnetically labeled $CD34^+$ cells), is isolated from blood diluted 20% with buffer to reduce viscosity, a 15 ml conical test tube may be employed as the separation vessel in an appropriate quadrupole magnetic device. After appropriate washes and/or separations and resuspensions to remove non-bound cells, $CD34^+$cells can very effectively be resuspended in a volume of 200 $\mu l$. This can be accomplished, for example, by starting with 12 ml of solution (blood, ferrofluid and dilution buffer) in a 15 ml conical test tube, performing a separation, discarding the supernatant and subsequent wash supernatants and resuspending the recovered cells in 3 ml of appropriate cell buffer. A second separation is then performed which may include additional separation/wash steps (as might be necessary for doing labeling or staining reactions) and finally the isolated cells are easily resuspended in a final volume of 200 $\mu l$. By reducing volume in this sequential fashion and employing a vortex mixer for resuspension, cells adhered to the tube above the resuspension volume are recovered into the reduced volume. When done carefully and rapidly in appropriately treated vessels, cell recovery is quite efficient (70–90%).

The efficiency with which magnetic separations can be done and the recovery and purity of magnetically labeled cells will depend on many factors. These include such considerations as: the numbers of cells being separated, the density of characteristic determinants present on such cells, the magnetic load per cell, the non-specific binding of the magnetic material (NSB), the technique employed, the nature of the vessel, the nature of the vessel surface, and the viscosity of the medium. If non-specific binding of a system is relatively constant, as is usually the case, then as the target population decreases so does the purity. For example, a system with 0.2% NSB that recovers 80% of a population which is at 0.25% in the original mixture will have a purity of 50%. Whereas if the initial population was at 1.0%, the purity would be 80%.

It is important to note that the smaller the population of a targeted cell, the more difficult it will be to magnetically label and recover. Furthermore, labeling and recovery are markedly dependent on the nature of the magnetic particle employed. As an example, large magnetic particles, such as Dynal beads, are too large to diffuse and effectively label cells in suspension through collisions created by mixing of the system. If a cell is in a population of 1 cell per ml of blood, or even less, as could be the case for tumor cells in very early cancers, then the probability of labeling target cells will be related to the number of magnetic particles added to the system and the length of time of mixing. Since mixing of cells with such particles for substantial periods of time will be deleterious, it becomes necessary to increase particle concentration as much as possible. There is, however, a limit to the quantity of magnetic particles that can be added. Instead of dealing with a rare cell mixed in with other blood components, one contends with a rare cell mixed in with large quantities of magnetic particles upon separation. The latter condition does not markedly improve the ability to enumerate such cells or examine them. Hence, the compromise is to limit the quantity of magnetic material and the mixing times, while enabling isolation of very rare target entities.

Another drawback to the use of large particles to isolate cells in rare frequencies (1 to 25–50 per ml of blood) is that large particles tend to cluster around cells in a cage-like fashion making them difficult to "see" or to analyze. Hence, the particles must be released before analysis, which clearly introduces other complications.

In theory, the use of colloidal magnetic particles in conjunction with high gradient magnetic separation appears to be the method of choice for separating a cell subset of interest from a mixed population of eukaryotic cells, particularly if the subset of interest comprises a small fraction of the entire population. With appropriate magnetic loading, sufficient force is exerted on a cell such that it could be isolated even in a media as viscous as that of moderately diluted whole blood. As noted, colloidal magnetic materials below about 200 nm will exhibit Brownian motion that markedly enhances their ability to collide with and magnetically label rare cells. This is demonstrated, for example, in U.S. Pat. No. 5,541,072 where results of very efficient tumor cell purging experiments are described employing 100 nm colloidal magnetic particles (ferrofluids). Just as important, colloidal materials at or below the size range noted do not generally interfere with viewing of cells. Cells so retrieved can be examined by flow cytometry or by microscopy employing visible or fluorescent techniques. Because of their diffusive properties, such materials, in contrast to large magnetic particles, readily "find" and magnetically label rare events such as tumor cells in blood.

There is, however, a significant problem associated with the use of ferrofluid-like particles for cell separation in external field gradient systems which, for reasons given above, are the device designs of choice. Direct monoclonal antibody conjugates to sub-micron size magnetic particles of the type described by Owen or Molday, such as those produced by Miltenyi Biotec, do not have sufficient magnetic moment for use in cell selection methods employing the best available external magnetic gradient devices, such as the quadrupole or hexapole magnetic devices described in U.S. Pat. No. 5,186,827. When used for separations in moderately diluted whole blood, they are even less effective. Using similar materials which are substantially more magnetic, such as those described in U.S. Pat. No. 5,597,531 to Liberti and Pino, more promising results have been obtained. In model spiking experiments, it has been found that SKBR3 cells (breast tumor line), which have a relatively high epithelial cell adhesion molecule (EpCAM) determinant density, are efficiently separated from whole blood with direct conjugates of anti-EpCAM ferrofluids even at very low spiking densities (1–5 cells per ml of blood). On the other hand, PC3 cells (a prostate line) which have low EpCAM determinant density are separated with significantly lowered efficiency. Most likely this is a consequence of inadequate magnetic loading onto these low determinant density cells.

In light of the foregoing, the present inventors have appreciated a need for methods directed at increasing or enhancing the "loading" of magnetic particles, whether large, small or colloidal, onto biological entities of interest. These methods may be used to advantage to isolate target substances or cells having low determinant density. Enhancing the efficiency of target bioentity isolation in turn facilitates subsequent biochemical and histochemical analysis of such entities.

SUMMARY OF THE INVENTION

It is the object of this invention to provide an efficient method for enhancing the interactions between specific binding pair members by systematically forcing collisions between the pair members present in a biological solution in a controlled and optimized fashion. This is accomplished by creating motion of one specific binding pair member relative to the other member such that increased numbers of collisions will occur. At the microscopic level, it appears that vigorous stirring of a solution may not always result in optimal numbers of collisions between members of a specific binding pair. For example, colloidal magnetic nanoparticles conjugated to monoclonal antibodies specific for a cell surface determinant, when mixed with target cells to be magnetically labeled, will label such cells much more efficiently and at a higher labeling density when the two entities are moved relative to each other. Thus, if cells are in suspension and the magnetic colloid is "pulled" through the cells, substantially greater numbers of nanoparticles are specifically bound to cells as compared to continued stirring, vortexing, and other means of mixing. Alternatively if the magnetic colloid is stable to centrifugation, then the cells may be moved through the colloid by centrifugation. This process also significantly increases the quantity of colloidal nanoparticles specifically bound to target cells. Hence the principle can be used in place of mixing or in addition to it.

There are many ways in which to induce motion of one entity relative to the other. In the examples provided below, magnetic gradients are used to translate particles through a suspension of cells; or centrifugation is used to move cells through gravitationally stable colloidal magnetic particles. Clearly in the latter case, neither component needs to be magnetic. For example, cells could be centrifuged through any colloid stable to the g-force of the process, such as centrifuging cells through colloidal gold.

In addition to ways for causing relative translation of the specific binding pair members mentioned above, charge or charge differential of one component relative to the other can be employed, as can any differential including magnetic or gravitational forces. One could envision an oscillating electrical field that would cause one entity to oscillate through the media relative to some other component. Similarly inertial forces may be employed There are numerous applications where the methods of the invention are used to advantage, including but not limited to, immunoassay, cell separation, protein isolation for analytical use or for bioprocessing, bacteria capture, and nucleic acid manipulation. There are industrial processes where two entities must bind or collide to form a product or a product intermediate. This invention may be used to reduce the time of incubation or lower the temperature of the reaction, as temperature is frequently used to accelerate such reactions. The methods of the invention effectuate efficient specific binding pair member interactions desirable for the various applications set forth above. In the case of magnetic separations, bioentities having low determinant density are captured due to the increased magnetic loading of ligand specific particles made possible by this invention. Furthermore, the invention should provide enormous benefit by permitting the use of reduced concentrations of one of the specific binding pair members. If magnetic particles (or any other agent) can be brought into contact in some repeated fashion with a target entity associated with one specific binding pair member, then a lesser amount should be required to achieve the same level of labeling.

As used herein, the term "target bioentities" or "analyte" refers to a wide variety of materials of biological or medical interest. Examples include hormones, proteins, peptides, lectins, oligonucleotides, drugs, chemical substances, nucleic acid molecules, (RNA or DNA) and particulate analytes of biological origin, which include bioparticles such as cells, viruses, bacteria and the like. The term "determinant" when used in reference to any of the foregoing target bioentities, may be specifically bound by a biospecific ligand or a biospecific reagent, and refers to that portion of the target bioentity involved in, and responsible for, selective binding to a specific binding substance whose presence is required for selective binding to occur. In fundamental terms, determinants are molecular contact regions on target bioentities that are recognized by receptors in specific binding pair reactions. The term "specific binding pair" as used herein includes antigen-antibody, receptor-hormone, receptor-ligand, agonist-antagonist, lectin-carbohydrate, nucleic acid (RNA or DNA) hybridizing sequences, Fc receptor or mouse IgG-protein A, avidin-biotin, streptavidin-biotin, and virus-receptor interactions. Various other determinant-specific binding substance combinations can conceivably be used in practicing the methods of this invention, as will be apparent to those skilled in the art. The term "antibody" as used herein, includes immunoglobulins, monoclonal or polyclonal antibodies, immunoreactive immunoglobulin fragments, and single chain antibodies. Also contemplated for use in the invention are peptides, oligonucleotides, or a combination thereof which specifically recognize determinants with specificity similar to traditionally generated antibodies. The term "detectably label" is used herein to refer to any substance whose detection or measurement, either directly or indirectly, by physical or chemical means, is indicative of the presence of the target bioentity in the test sample. Representative examples of useful detectable labels, include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules. The phrase "to the substantial exclusion of" refers to the specificity of the binding reaction between the biospecific ligand or biospecific reagent and its corresponding target determinant. Biospecific ligands and reagents have specific binding activity for their target determinant yet may also exhibit a low level of non-specific binding to other sample components.

BRIEF DESCRIPTION OF THE DRAWINGS

FIGS. 5A and 5B are at 10×magnification; FIGS. 5C and 5D are at 20×magnification.

FIG. 7A: no free ferrofluid present during magnetic separation; FIG. 7B: specific ferrofluid present during magnetic separation; FIG. 7C: non-specific ferrofluid present during magnetic separation.

DETAILED DESCRIPTION OF THE INVENTION

From the foregoing discussion, it should be clear that any means for enhancing binding interactions between members of specific binding pairs improves the separability of analytes bearing one or the other of such members. In commonly owned patent application entitled "Methods of Controlled Aggregation of Magnetic Nanoparticles" of Liberti et al., means for increasing the magnetic load onto target entities via an agglomeration principle is disclosed. That disclosure is based on the discovery of a specific factor, believed to be an IgM, which occurs at varying levels in human blood from about 85% of the normal population. This IgM-like factor, reacts with ferrofluids prepared by methods described U.S. Pat. No. 5,597,531 to Liberti and Pino. The ferrofluid aggregating factor (FFAF) causes additional ferrofluid to cluster onto ferrofluid already bound to cells. This additional magnetic loading significantly enhances the efficiency of rare cell isolations, particularly isolation of low determinant density cells. These observations also facilitated the development of methods for reversing clustering of ferrofluids such that cells are not damaged and cell recoveries are enhanced. The preferred sequence is (1) remove or disable any endogenous FFAF(s) in blood of which there are potentially many; (2) incubate cells with ferrofluid conjugated to a determinant specific ligand; (3) either simultaneously with step 2 or sequentially cause ferrofluid agglomeration by adding a reversible agglomerating agent; (4) subject the sample to a magnetic gradient to cause isolation of the target; and (5) reverse the agglomeration with at least one cell compatible deagglomerating agent. This procedure results in efficient and reproducible isolation of rare low determinant density cells from whole blood. By washing blood free of endogenous FFAF it should be apparent that step 1 can be eliminated and that recovery will be enhanced. When performing labeling experiments, it is customary to incubate the target substance with a labeling agent. The period of incubation will depend on several factors. These include the size and concentration of the labeling agent, the temperature of the assay and on whether or not the system is mixed. In the case of labeling cells with monoclonal antibodies at concentrations of 1–2 $\mu$g/ml, it is common to incubate the target substance with the labeling ligand for 15 minutes at room temperature, depending on antibody affinity. By increasing the concentration of antibody to 5 $\mu$g/ml, incubation times can be shortened to about 5 minutes. In either case, mixing of the sample has no demonstrable effect on the amount of antibody bound. In the case of large magnetic particles, such as Dynal beads, incubation times recommended by the manufacturer are from 20 to 30 minutes, with mixing required to prevent settling. It has been found that ferrofluid labeling requires a 15 minute incubation followed by a standardized separation of 15 minutes in a quadrupole separator (U.S. Pat. No. 5,186,827), which typically gives the best results. Most likely this is a consequence of ferrofluid colloidal stability, size and colloidal properties.

In studies on isolation of cells from viscous solutions (typically blood), it has been routinely observed that optimal separation from the media may take 10–15 minutes in one of the quadrupole magnetic devices mentioned above. However, if magnetically collected cells are resuspended in a buffer and are again separated, the optimum time for such processing takes approximately 3 to 4 minutes. This observation cannot be explained by viscosity effects alone. Experiments were performed to assess isolation of low determinant density epithelial tumor cells spiked into whole blood that had been treated to remove endogenous aggregating factors. Ferrofluid directly conjugated to an anti-EpCAM monoclonal antibody was employed. Immediately following a 15 minute room temperature incubation, the amounts of ferrofluid bound to cells were quantified and compared with the amount of labeling achieved after a combined incubation and a 10 minute separation step. The data reveal that in the absence of a magnetic separation step, the amount of ferrofluid bound to the target cells was reduced 5 fold. To assess whether incubation time affected ferrofluid binding, the first sample was incubated an additional 10 minutes at room temperature such that treatment times were the same between the two samples. No substantial increase in ferrofluid binding was observed upon longer incubation. If, immediately after the incubation step and before the separation step, a quantity of anti-EpCAM monoclonal antibody in an amount determined to prevent further binding of ferrofluid was added, it was found that the amount of ferrofluid bound to the separated cells was identical to that obtained after incubation alone. These observations suggested that the additional ferrofluid, which binds to cells during the separation step, is bound to specific cell determinants, and is not a type of ferrofluid-ferrofluid phenomena induced by magnetics. The studies presented in the following examples will prove that the above hypothesis is indeed correct.

Thus, novel methods are provided which may be applied to enhance interactions between any specific binding pair regardless of the size thereof. Only one specific binding pair member must be made to move relative to the other to induce enhanced binding of the specific binding pair members. As an example of the general applicability of the principle underlying this invention, when a cell suspension incubating with specific ferrofluid is centrifuged such that only the cells move in the centrifugal field (and not the ferrofluid itself), considerably more ferrofluid will be bound to the cells than would be the case if the suspension were thoroughly mixed with the ferrofluid. Larger Dynal beads, because of their size and density, centrifuge along with cells, and therefore cannot provide an identical magnetic loading phenomenon as that described herein. Thus, when Dynal bead-specific ligand conjugates are incubated with a cell suspension and the magnetic beads are made to move through the suspension in iterative cycles, by placing an appropriate magnet adjacent to the container, the amount of beads bound to cells is very significantly enhanced, as compared with simple mixing. These observations suggest that there are limitations to true mixing or mixing that includes collisions at the microscopic and perhaps the macromolecular level.

There are various ways of inducing motion of one specific binding pair member relative to the other, many of which do not require magnetic effects on either or both of the specific binding pair members. In a general sense, this invention has many practical advantages and applications. Greater specific binding pair interactions can be accomplished as compared with simple mixing or stirring. Additionally, in many instances it will be beneficial to accomplish optimal binding in a shorter time period. This invention will be applicable for that purpose, and will not only generally reduce the amount of specific binding pair member required, but will also greatly increase efficiency of any test or process wherein interactions between specific binding pair members is an important event. In addition to cell and cell-like separations, there are many other potential applications, such as immunoassay, capture of DNA or RNA and industrial processes, which will benefit by this invention. Magnetic separation methods in which magnetic particles are used for isolating substances of interest from a non-magnetic test medium by means of magnetic gradient separation are preferred. The sample is first mixed which allows the magnetic particles to find targets before placing in the magnetic separation device. During this incubation period, it is customary for the sample to be mixed or stirred by some means, such as vortexing, to cause greater contact between magnetic particles and target cells, as well as the prevention of the components from settling. In the examples described below it is demonstrated that the labeling of the substances of interest under the influence of a magnetic gradient which translates nanoparticles through the solution relative to the cells markedly increases the labeling density. The increase in labeling density results in a more efficient separation of the target substances.

For labeling bioentities such as cells, bacteria, viruses, proteins, or nucleic acids with magnetic particles, different sized particles can be used. However, translation of the magnetic particle through the solution or suspension to be labeled must be carried out in a manner that optimizes collisions and binding. If magnetic gradients are used to translate the particles, then gradients which cause the particles to collide with, but not "rip" determinants (e.g., receptors) from the target bioentities, are preferred. Hence, Dynal particles require low gradient fields, whereas higher magnetic gradients may be utilized with colloidal nanoparticles. Differential movement of target and collecting substances during labeling reactions can be effectuated during the separation step, or by repeated separations or partial separations and resuspensions. Alternatively, magnetic materials can be translated multidirectionally within the incubation vessel. Where centrifugation is used to effect relative translation, one of the specific binding pair members should be unaffected by the centrifugal force or the differential of the centrifugal forces acting on the members of the specific binding pair should be sufficient to cause collisions.

The following examples further describe in some detail the basic principle underlying this invention and various means for employing the invention as it relates to magnetic separations. The use of colloidal magnetic nanoparticles (ferrofluids) for cell separations constitutes the best mode contemplated by the inventors as of the time of present disclosure. These particular examples should in no manner be regarded as limiting the invention.

EXAMPLE 1

Figure 1A:
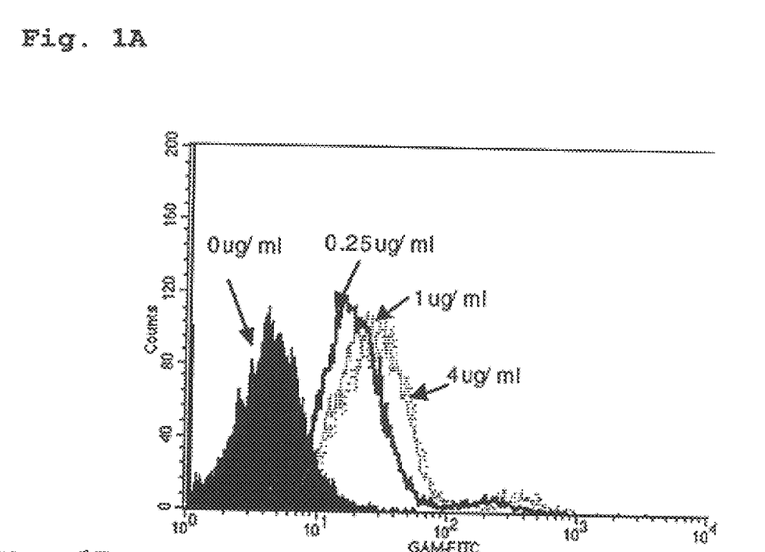
FIG. 1A is a histogram and FIG. 1B is graph showing the labeling of PC3 cells with EpCAM specific monoclonal antibodies.
Figure 1B:
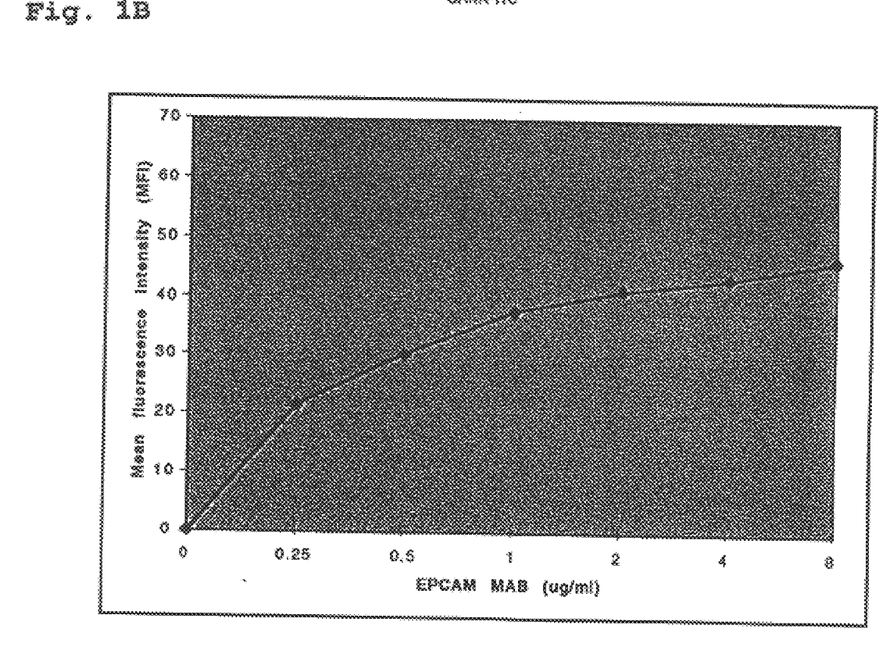

Cell Labeling with a Cell Specific Monoclonal Antibody in the Absence of Ferrofluid The Epithelial cell adhesion molecule (EpCAM) is an exemplary target antigen and has been utilized to demonstrate the enhanced magnetic loading onto target bioentities in accordance with the methods of the present invention. EpCAM is expressed on cells of epithelial cell origin but not on cells of hematopoietic origin. The density of the EPCAM antigen depends on the cell type to be isolated and/or analyzed. For example, while expression of the EpCAM on the prostate tumor cell line (PC3 cells) is homogeneous, the level of expression is relatively low. FIG. 1A is a histogram showing the distribution of EpCAM on PC3 cells using a mouse monoclonal antibody specific for EpCAM. The level of EpCAM antibody binding was in turn quantified with a secondary goat anti-mouse antibody (GAM) conjugated to fluorescein isothiocynate (FITC) GAM-FITC. The fluorescence A intensity is directly proportional to the amount of antibody on cells. The histogram in FIG. 1 shows the fluorescence intensity of the PC3 cells which represents the distribution of EpCAM on the cells. FIG. 1A also shows that the PC3 cells consist of one population of cells with respect to EpCAM. Saturation of the antigen is obtained at a concentration of 4 $\mu$g/ml of EPCAM monoclonal antibody as shown in FIG. 1B.

EXAMPLE 2

Cell Labeling with Anti-EpCAM-ferrofluid in the Absence of Relative Magnetic Translational Motion The mouse monoclonal antibody specific for EpCAM was coupled to magnetic nanoparticles (ferrofluids). The PC3 cells were incubated with the epithelial cell specific ferrofluids (anti-EpCAM-FF) at concentrations of 5, 10, 20, 40 and 60 $\mu$g of iron (Fe) per ml. If it is assumed that all of the antibody coupled to the ferrofluids is able to specifically bind to target, the approximate antibody concentration is 0.4, 0.8, 1.5, 3.1 and 4.6 $\mu$g per ml respectively. In the experiment, approximately 200,000 PC3 cells in 0.75 ml of an isotonic buffer were added to a 12×75 mm polystyrene tube. Anti-EpCAM-FF (20 $\mu$l volume) was added to the sample at a final concentration of 5, 10, 20, 40 and 60 $\mu$g/ml. The samples were mixed by gentle vortex. After incubation for 15 minutes, the samples were centrifuged at 500 g for 5 minutes to remove the cells from unlabeled ferrofluid. As noted above and shown later, this step enhances ferrofluid loading onto cells. For the purposes of this example, the added ferrofluid loaded on by that step will not affect the overall results. The supernatant was discarded. The cell pellet was resuspended in 100 $\mu$l of an isotonic buffer. The cells were then stained with GAM-FITC to quantify the amount of anti-EpCAM-FF bound to cells. After incubation for 15 minutes, 1 ml of an isotonic buffer was added to the cells and the sample centrifuged to remove excess GAM-FITC. The cell pellet was resuspended in 500 $\mu$l of an isotonic buffer and fluorescence intensity of the cells was determined by flowcytometry (FACScaliber, Becton-Dickinson, San Jose, Calif.). The observed fluorescence intensity was directly proportional to the amount of ferrofluid on cells.

Figure 2A:
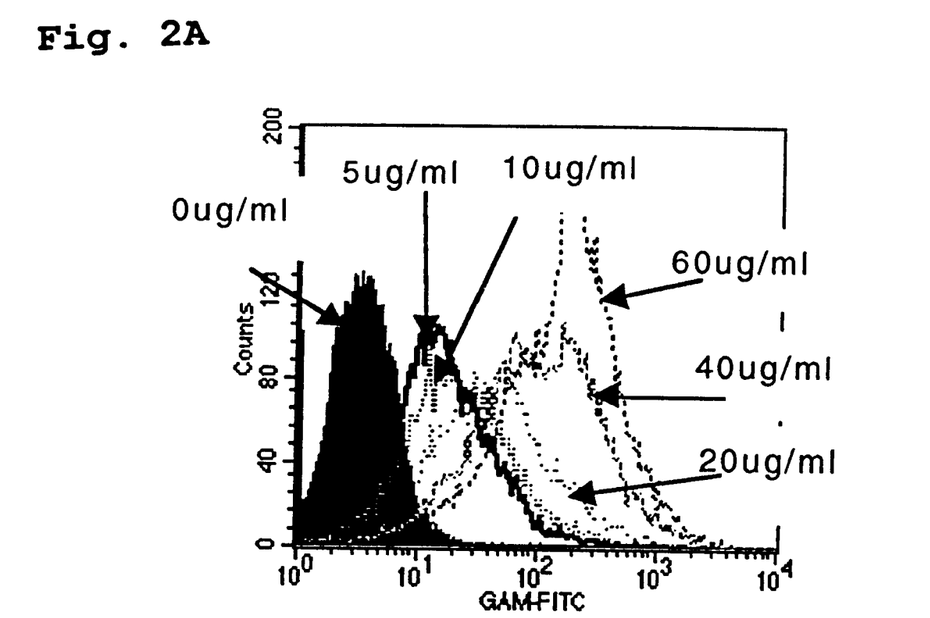
FIGS. 2A and 2B are a pair of histograms showing labeling of PC3 cells with magnetic nanoparticles conjugated to EpCAM specific monoclonal antibodies at different concentrations. Labeling of cells is shown before (FIG. 2A) and after (FIG. 2B) magnetic separation.

FIG. 2A shows fluorescence histograms. The mean fluoresence intentity (MFI) or baseline fluorescence of the unstained cells was 4.1 in arbitrary units. The MFI at a concentration of 5 $\mu$g/ml of anti-EpCAM-FF was 22.4. The MFI at a concentration of 10 $\mu$g/ml was 33.7. The MFI at a concentration of 20 $\mu$g/ml was 67.3. The MFI at a concentration of 40 $\mu$g/ml was 153.0. The MFI at a concentration of 60 $\mu$g/ml was 220.3. From the data of FIG. 2A it is clear that a titration curve for ferrofluid could be obtained which is similar to that obtained when purified antibody is used to label cells as shown in FIG. 1A.

The relatively large amounts of ferrofluids (60 $\mu$g/ml) required to saturate the cells as shown in FIG. 2A, places constraints on the economic viability of the procedure in the case where larger volumes need to be processed. If one is working with a whole blood sample, e.g., 20 ml, which is to be reduced to 200 $\mu$l to perform the analysis, there is another complication. The amount of free ferrofluid present after sample volume reduction can interfere with the subsequent analysis. It is therefore desirable that magnetic particle concentration be kept to a minimum while at the same time providing for optimal labeling and efficient separation.

EXAMPLE 3

Labeling Intensity of Cells with a Cell Specific or Nonspecific Ferrofluid Before and After Magnetic Separation This example and, several which follow, demonstrates how the relative motion principle was discovered, as well as the magnitude of the effect and its consequences. In this experiment, cells of the prostate tumor cell line PC3 having low EpCAM determinant density were used. Approximately 500,000 PC3 cells in 1.5 ml of an isotonic buffer were added to a 12×75 mm polystyrene tube. Anti-EpCAM-FF (20 $\mu$l volume) was added to the sample at a final concentration of 0, 5, 10, 20, 40 and 60 $\mu$g/ml. The samples were mixed by gentle vortex and placed in quadrupole magnetic separators for 10 minutes to effect separation. After 10 minutes the supernatant was discarded. The tubes were removed from the magnetic separators. The cells and free ferrofluid collected at the vessel walls were resuspended in 1 ml of isotonic buffer by vortexing. The sample was centrifuged as above to remove cells from free ferrofluid. The cell pellet was resuspended in 100 $\mu$l of an isotonic buffer containing saturating amounts of GAM-FITC. After incubation for 15 minutes, 1 ml of an isotonic buffer was added to the tube and centrifuged to remove excess GAM-FITC. The cell pellet was resuspended in 500 $\mu$l of an isotonic buffer and fluorescence intensity of the cells was determined by flowcytometry.

Figure 2B:
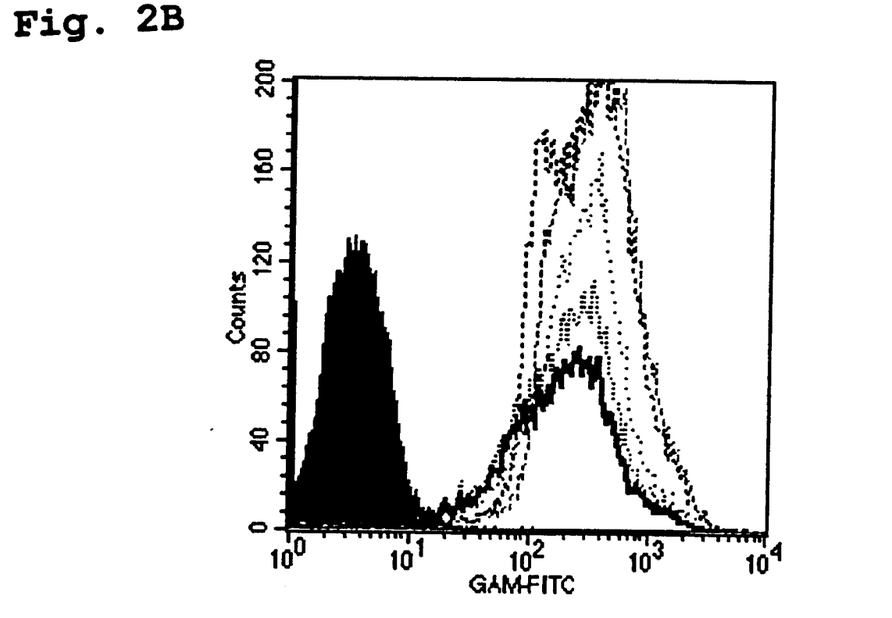

The histograms shown in FIG. 2B show that, in contrast to FIG. 2A, the labeling of the PC3 cells with ferrofluids was relatively uniform at all concentrations of ferrofluids tested following separation of the ferrofluid-labeled PC3 cells in a magnetic field. Furthermore, the labeling in each case was similar to that obtained with the highest level of ferrofluid used in the experiment of FIG. 2A, i.e., the experiment in which no magnetic separation took place.

Figure 3A:
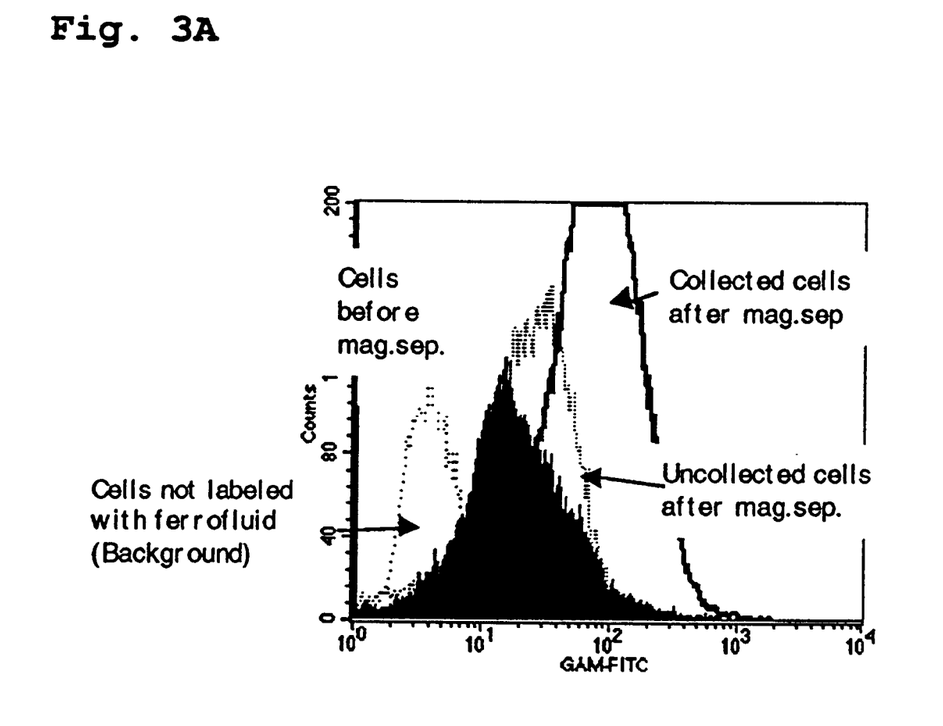
FIGS. 3A and 3B are histograms showing the labeling of PC3 cells with a cell specific monoclonal antibody conjugated to ferrofluid (FIG. 3A) compared to labeling obtained with a nonspecific monoclonal antibody conjugated ferrofluid (FIG. 3B) In each case the fluorescence intensity of PC3 cells before and after magnetic separation is shown.

To examine the reason for the enhanced labeling of the magnetically collected cells upon incubation in the magnetic separator, the following experiments were done. Anti-EpCAM-FF (20 µl volume) was added to the PC3 cell sample at a final concentration of 5 µg/ml and a volume of 1.5 ml. After incubation for 15 minutes, 500 µl of the ferrofluid-labeled cells were transferred to a 12×75 mm polystyrene tube and centrifuged at 500 g for 5 minutes to remove cells from unlabeled ferrofluid. The remaining 1 ml of ferrofluid-labeled cells were placed in a quadrupole magnetic separator for 10 minutes. After aspirating the supernatant, the collected cells and free ferrofluid were resuspended in 1 ml of an isotonic buffer and centrifuged as above to separate the cells from free ferrofluid. After the respective centrifugation, supernatants were discarded and cell pellets were resuspended in 100 µl of cell buffer and labeled with GAM-FITC. After incubation for 15 minutes, 1 ml of an isotonic buffer was added to the tube and centrifuged to remove excess GAM-FITC. The cell pellets were resuspended in 500 µl of an isotonic buffer and fluorescence intensity of cells determined by flowcytometry. Additionally, after the magnetic separation experiment, the uncollected cells which remained in the buffer were transferred to a 12×75mm tube, centrifuged to separate cells from any free ferrofluid, and stained with GAM-FITC as described above. FIG. 3A shows histograms of the fluorescence intensity of cells not exposed to the anti-EpCAM-FF, cells incubated with the anti-EpCAM-FF before separation, and the uncollected and collected cell fraction after magnetic incubation. The mean fluorescence intensity (MFI) was 5.0 for unlabeled cells (background fluorescence), 19.4 for the ferrofluid labeled cells before magnetic separation, 69.5 for the cells obtained after magnetic selection and 28.2 for the cells which remained in suspension after magnetic selection. The data shows that MFI of the collected cells was 4-fold higher when compared to the same cells before magnetic separation. The MFI of the uncollected cells was slightly higher than the cells before magnetic separation. FIG. 3A clearly illustrates that although the PC3 cells are homogenous with respect to EpCAM density after magnetic separation, the magnetically collected cells have significantly more ferrofluid on their surfaces as compared to the uncollected cells. The cells not collected during separation have only a slightly larger quantity of ferrofluid on their cell surfaces as compared to the cells that were labeled with ferrofluid but not exposed to the magnetic separator.

Figure 3B:
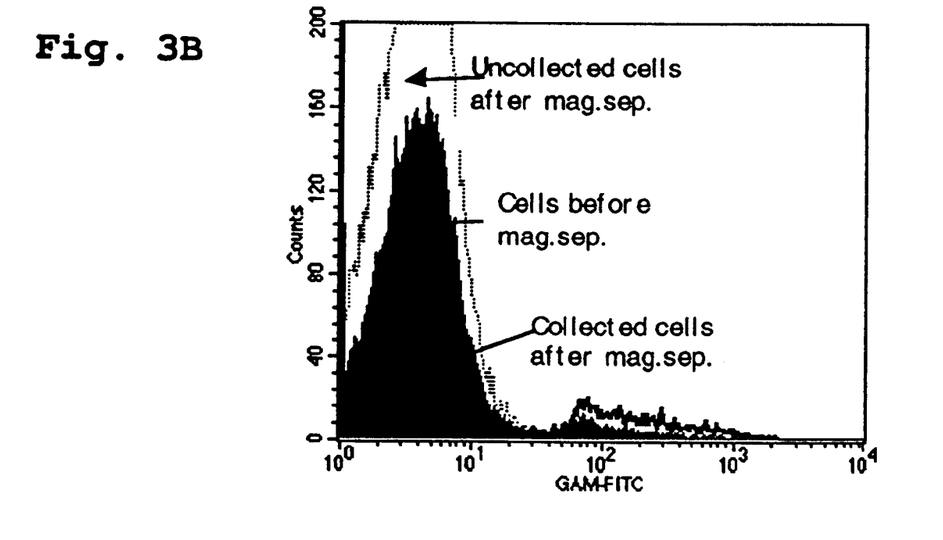

To be certain that this increase in ferrofluid labeling is due to specific ferrofluid-receptor interactions, the experiment was repeated using ferrofluids labeled with nonspecific antibodies which recognize the CD34 antigen (CD34 FF), an antigen not present on PC3 cells. FIG. 3B shows histograms of the fluorescence intensity of PC3 cells in the absence of anti-CD34-FF, cells incubated with the anti-CD34-FF before separation, and the uncollected and collected cell fraction after magnetic incubation. The mean fluorescence intensity (MFI) was 5.0 for unlabeled cells (background fluorescence), 4.8 for the ferrofluid labeled cells before magnetic separation, 4.5 for the cells which remained in suspension after magnetic selection and 17.1 for the few cells which were nonspecifically selected. In contrast with the experiments using the anti-EpCAM-FF, the cells were not labeled with the secondary GAM-FITC conjugated antibody, indicating that no ferrofluids were present on the cells.

Conclusions that can be drawn from the above experiment are: 1) following addition of ligand specific ferrofluids to the sample, subsequent exposure to a magnetic field gives rise to an increase in the number of magnetic particles bound to cells; 2) magnetically collected cells have a larger number of magnetic particles on the cell surface as compared to the uncollected cells, although they express a similar number of the EpCAM antigen as illustrated in FIG. 1; and 3) the increase in magnetic mass per cell can only be obtained with cell specific ferrofluids.

EXAMPLE 4

Increase in Labeling Density can be Obtained with Different Antigens

Figure 4:
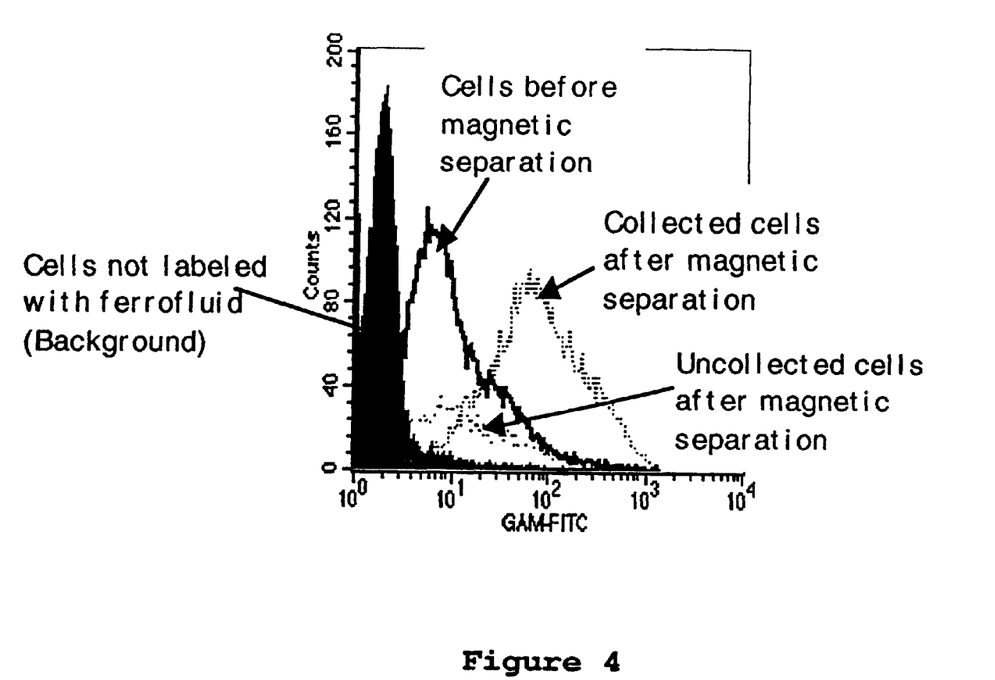
FIG. 4 is a histogram showing labeling of KG1a cells with magnetic nanoparticles conjugated to CD34 specific monoclonal antibodies before and after magnetic collection.
Figure 5A:
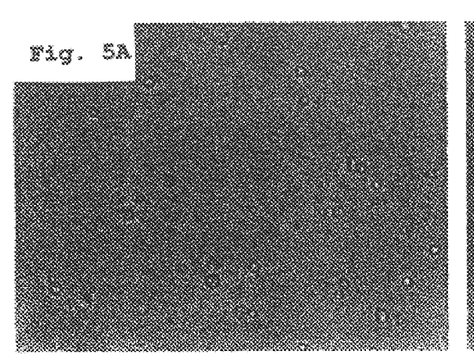
FIGS. 5A–5D are a series of micrographs showing prostate tumor (PC3) cells after incubation with Dynal anti-epithelial cell beads outside (FIGS. 5A and 5C) and (FIGS. 5B and 5D) inside magnetic field. Small dots are free Dynal beads.
Figure 5B:
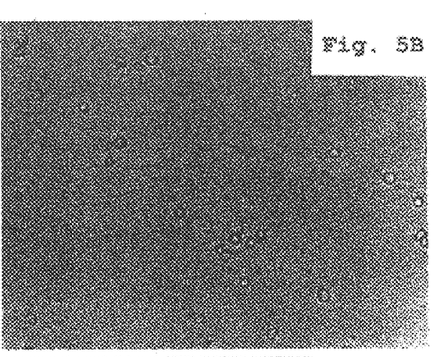
Figure 5C:
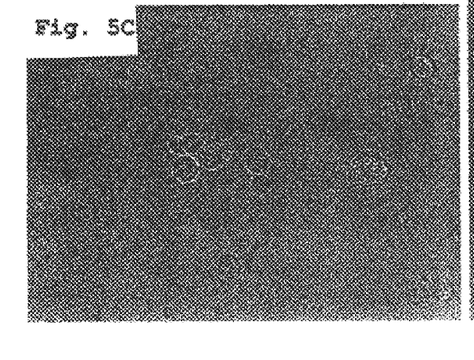
Figure 5D:
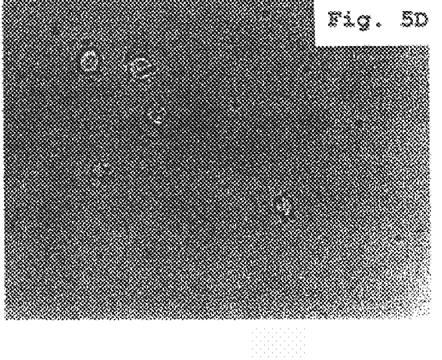
Figure 6A:
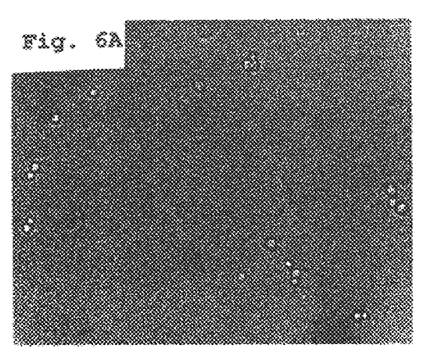
FIGS. 6A–6D are a series of micrographs showing breast tumor (SKBR3) cells after incubation with Dynal anti-epithelial cell beads outside and inside magnetic field. Small dots are free Dynal beads.
Figure 6B:
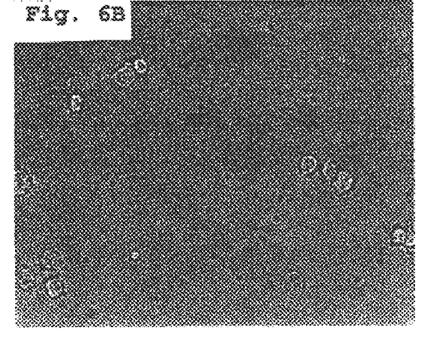
Figure 6C:
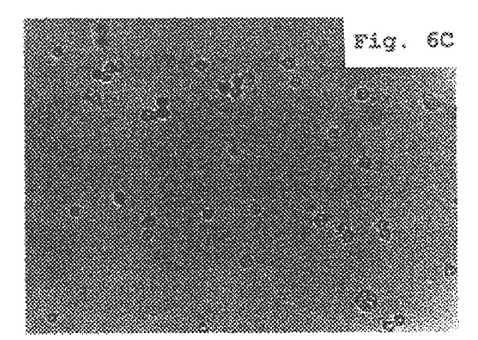
Figure 6D:
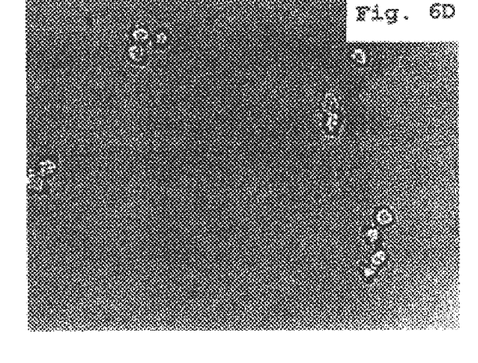

To demonstrate that the phenomenon described herein is not restricted to a particular antigen determinant present on a tumor cell, the experiments were conducted using the CD34+ KG1a cell line and a ferrofluid to which the CD34 monoclonal antibody was conjugated. The experimental procedure used in this experiment was similar to that described for PC3 cells and anti-EpCAM-FF discussed above. The results of this experiment are shown in FIG. 4. The data reveal that magnetic separation resulted in an increase in the amount of magnetic particles binding to target cells. The mean fluorescence intensity (MFI) was 2.1 for unlabeled cells (background fluorescence), 16.7 for the ferrofluid labeled cells before magnetic separation, 125.1 for the cells obtained after magnetic selection and 20.2 for the cells which remained in suspension after magnetic selection. These results are consistent with the results obtained for EpCAM antigen positive cells.

EXAMPLE 5

Relative Translation Induced Increase in Labeling Density is Independent of Particle Size The above examples show that an increase in labeling of cells with specific magnetic nanoparticles can be obtained during the separation process when magnetic particles are moving relative to target cells. The magnetic nanoparticles used above are ferrofluids in 150–180 nm size range. To address whether or not this phenomena applies to a larger size of magnetic particles, experiments were performed using Dynal beads. Dynal (Norway) manufactures magnetic beads in two different sizes (2.8 and 4.5 µm) which are used for isolation of cells. In this example, anti-epithelial cell Dynabeads were used which were 2.8 µm in size and coated with a mouse monoclonal antibody (Ber-EP4) specific for EpCAM. As these beads can be seen under a microscope, secondary staining (e.g., with GAM-FITC) is not required to quantify the amount of beads bound to cells. Isotonic buffer (0.75 ml) containing 400,000 prostate tumor cells (PC3) was added to a 12×75 mm polystyrene tube. PBS buffer (50 µl) containing anti-epithelial cell specific Dynabeads ($1 \times 10^6$ beads) was added to the sample, mixed well by vortexing and the sample placed near a single pole magnetic separator for 10 minutes. Every 2 minutes, the sample was taken away from the magnetic separator, mixed and returned. The magnetic gradient employed for this experiment was such that the Dynal beads would move slowly through the sample. As a control, another sample containing PC3 cells was incubated with Dynabeads by mixing in the absence of a magnetic field also for 10 minutes. From each of these samples manipulated for 10 minutes, 5 µl were spotted onto a microscope slide. The cells and free Dynabeads were then photographed using a microscope with a digital camera attached to it.

FIG. 5 shows PC3 tumor cells bound to magnetic beads and free beads. FIGS. 5A and 5C show samples which were mixed, but not exposed to a magnetic field. Note the significant numbers of free Dynabeads. In FIGS. 5B and 5D very few free beads are observed in the sample as the Dynabeads and cells had been exposed to a magnetic gradient. There are also clearly more beads bound per cell in the latter case. These results show that incubation of target cell containing samples with larger size magnetic beads results in a significant increase in binding of the magnetic beads to the cells, provided the beads are caused to move through the cell sample. The experiment was repeated with anti-epithelial Dynabeads using the high EpCAM density breast cancer cell line, SKBR3 and the results are shown in FIG. 6. These results are consistent with those observed for PC3 cells, i.e. more beads were bound to cells and no free beads were observed in the sample that had been subjected to a magnetic field when compared to those samples which were merely mixed.

EXAMPLE 6

Figure 7A:
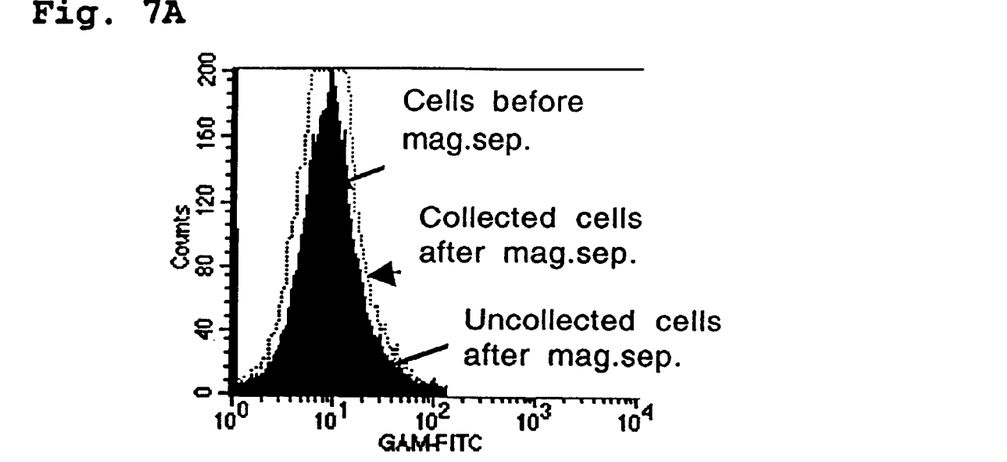
FIGS. 7A–7C are histograms showing labeling of PC3 cells with a specific or nonspecific ferrofluid during magnetic separation.
Figure 7B:
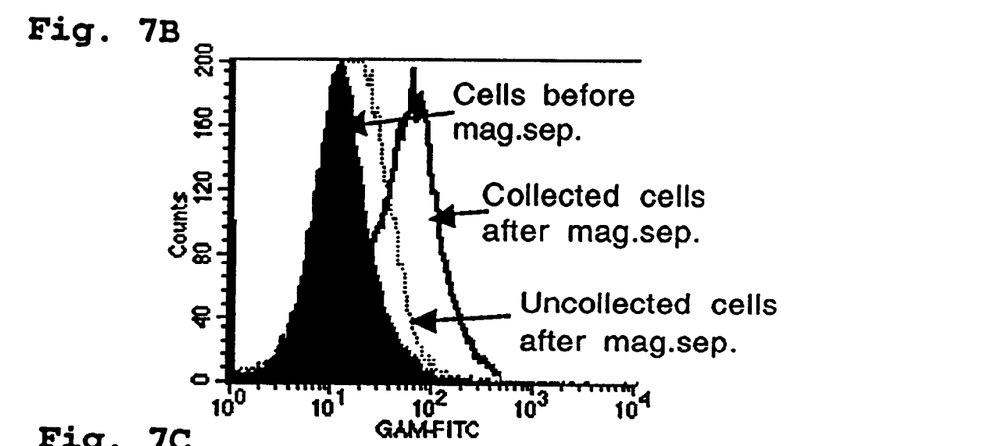
Figure 7C:
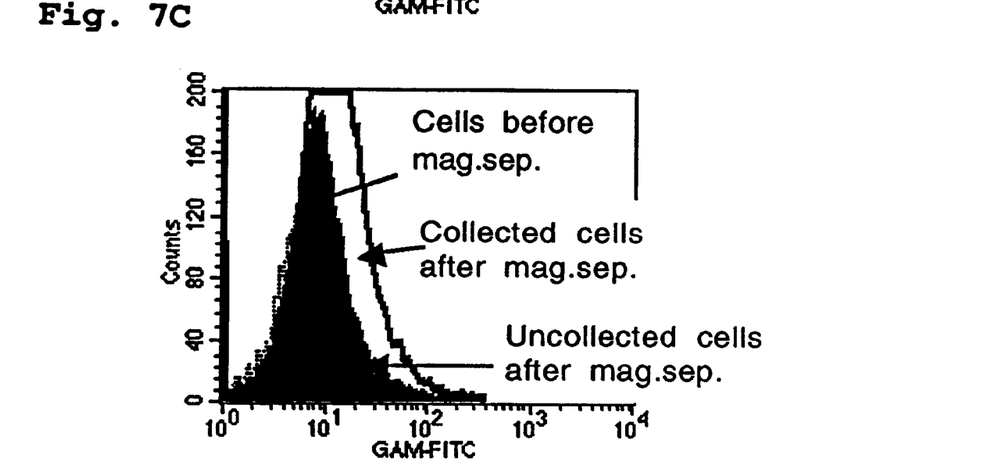

Labeling Intensity of Cells After Incubation with a Cell Specific Ferrofluid Before and After Magnetic Separation To further confirm the principle described herein, and to determine whether or not ferrofluid free in solution is necessary to obtain the observed increase in cell labeling, the following experiments were conducted. The experiments were performed with the prostate tumor cell line PC3 using anti-EpCAM-FF and anti-CD34-FF. FIG. 7A shows a histogram of the fluorescence intensity of PC3 cells obtained after incubation with anti-EpCAM-FF both before and after magnetic separation. In contrast with the experiments shown in FIG. 3, the cells were removed from ferrofluid free in solution by centrifugation before magnetic separation. As is clear from FIG. 7A, the labeling density did not increase during the magnetic separation, indicating the need for free ferrofluid during magnetic separation. In FIG. 7B the experiment was repeated with the anti-EpCAM-FF added at a concentration of 2 µg/ml before the magnetic separation. In this case, the labeling of the collected cells clearly increased. If, however, anti-CD34-FF was added before separation, no increase in the labeling intensity of the cells was observed. This further demonstrates that the ferrofluid free in solution needs to be specific for the target cells in order to obtain the increased labeling of the cells, as shown in FIG. 3 and Table I below. Hence, the magnetic gradient acts to move ferrofluid relative to cells so as to promote specific binding.

TABLE I

| Free, excess ferrofluid present during magnetic separation | Mean fluorescence intensity (MFI) of PC3 cells | |
|---|---|---|
| | Cells before magnetic cells separation | Collected after magnetic separation |
| None | 11.9 | 20.4 |
| Specific EpCAM MAb | 15.7 | 65.4 |
| Nonspecific MAb | 11.2 | 15.1 |

The following conclusions may be drawn from the above experiment: 1) magnetic separation does not increase labeling intensity if excess/unbound ferrofluid is removed prior to magnetic separation; and 2) the free ferrofluids in solution must be cell-type specific to increase labeling intensity of target bioentities.

EXAMPLE 7

Optimization for Increasing the Labeling Intensity and Separation Efficiency.

From the foregoing experiments, it is clear that the movement of specific magnetic particles relative to cell targets significantly augments the binding reaction. In this example, the labeling of tumor cells with a specific anti-EpCAM-FF under different incubation conditions was assessed to provide optimal conditions for the observed augmentation. An isotonic buffer (1 ml) containing 200,000 prostate cells (PC3) was added to different 12×75 mm polystyrene tubes. Specific anti-EpCAM-FF (20 µl) was added to each sample to final concentration of 5 µg/ml and each sample was mixed by vortexing. The samples were incubated under different conditions set forth in Table II. After a 15 minute incubation, the samples were mixed by vortexing and were centrifuged at 500 g for 5 minutes to remove cells from excess ferrofluid. The cell pellets were resuspended in 100 µl of an isotonic buffer after aspirating the supernatant. The cells were then stained with GAM-FITC and the fluorescence intensity of the cells determined by flowcytometry. The results are given below in Table II.

TABLE II

| Incubation conditions immediately following mixing | Mean fluorescence intensity with cells (MFI) | MFI (−) background MFI |
|---|---|---|
| Cells + GAM-FITC at room temperature 15 min. Background flluoresence) | 3.8 | — |
| cells + anti-EpCAM-FF vortexed 5 sec. every min. for 15 min. | 7.8 | 4 |
| cells + anti-EpCAM-FF in magnetic separator removed every minute., vortexed 5 sec. and replaced. Total 15 min. | 30.0 | 26.4 |

TABLE II-continued

| Incubation conditions immediately following mixing | Mean fluorescence intensity with cells (MFI) | MFI (−) background MFI |
|---|---|---|
| cells + anti-EpCAM-FF in magnetic separator removed every 5 min.., vortexed 5 sec. and replaced. Total 15 min. | 31.3 | 27.5 |
| cells + anti-EpCAM-FF in magnetic separator for 15 min. | 22.7 | 19.9 |

Labeling of target cells with ferrofluid increased significantly (5 to 7 fold) when cells were incubated with ferrofluid and exposed to a magnetic field in the quadrupole magnetic separator, i.e. while translation of ferrofluid is occurring. Note that when a very similar experiment was done in a uniform magnetic field, i.e., no magnetic gradient, the labeling obtained was identical to that obtained herein when cells and ferrofluid were incubated in the absence of any magnetic field.

EXAMPLE 8

Labeling of Target Cells by Moving Cells Through Ferrofluid by Gravitational Force The foregoing experiments show that movement of ferrofluid in the high gradient region in the magnetic field enhances ferrofluid binding to target cells, i.e., cells are labeled faster and more effectively. To demonstrate that the movement of target cells relative to the ferrofluid likewise results in increased binding of specific ferrofluid, a centrifugation experiment was performed. For this experiment target cells (PC3) were mixed with anti-EpCAM-FF as above and immediately centrifuged at 500 g for 5 minutes. Under these conditions ferrofluid does not redistribute noticeably. The labeling of cells with ferrofluid was checked after staining with GAM-FITC as described above. These experiments revealed that moving cells through ferrofluid by centrifugal force also gave rise to increased cell labeling by a factor of 2-fold when compared to cells subjected to static incubation. It is noteworthy that the means used to determine the amount of labeling employs centrifugation of cells away from unbound ferrofluid. Hence, all of the controls are artificially elevated. The data obtained, however, clearly demonstrate the principle of differential movement for increasing binding between specific binding pair members.

Conclusions that may be drawn from the above experiment are as follows: 1) it is the magnetic gradient, not the magnetic field strength present during the incubation, which effectuates the increase in labeling intensity. Hence, translation of the nanoparticles is required; 2) a significant increase in target cell labeling using sub-optimal concentrations of magnetic particles can be obtained by a) moving the target entities through the ferrofluid suspension or by b) moving the magnetic particles through the cell suspension.

EXAMPLE 9

Increase in the Number of Particles on the Cells Increases the Cell Recovery

The results of the experiment described hereinbelow further illustrate that increasing the loading of magnetic particles onto target bioentities using the methods of the present invention significantly enhances the collection efficiency of such entities. Blood (1 ml) was centrifuged and the plasma removed and replaced by an isotonic buffer to remove any potential components that could effect the labeling of the cells. The blood cells were added to a 12×75 mm polystyrene tube followed by 0.5 ml of dilution-wash buffer (Immunicon). Isotonic buffer (50 $\mu$l) containing a known number of low EPCAM density PC3 cells were spiked into the blood sample. 20 $\mu$l anti-EpCAM-FF were added to each sample to final concentration of 5 $\mu$g/ml.

One sample was incubated in the absence of any magnetic gradient for 15 minutes without mixing. After incubation, the sample was placed in a quadrupole magnetic separation device for 10 minutes to effect separation. The washed, collected cells were stained with labeled antibodies to determine the recovery of spiked tumor cells by flowcytometry as follows. A Her2-neu MAb conjugated to Phycoerythrin (PE) identifying the tumor cells and the peridinin chlorophyll protein (PerCP) conjugated CD45 MAb specific for leukocytes were added to the sample and incubated for 15 minutes. After staining, the cells were washed by magnetic separation in order to remove excess staining antibodies. The magnetically washed and collected cells were resuspended in 500 $\mu$l of dilution-wash buffer. A nucleic acid dye and 10,000 3 $\mu$m fluorescent beads in a 10 $\mu$l volume were added to the sample. The sample was then analyzed on a flowcytometer using the emitted fluorescence of the nucleic acid dye as a threshold. The fraction of the fluorescent beads acquired in the flowcytometer was used to determine the amount of sample analyzed by flowcytometry which in turn enables the calculation of the recovery of the spiked tumor cells.

After mixing cells and ferrofluid, a second sample was placed inside the quadrupole magnetic separation device for 15 minutes. At each minute, the tube was taken out the magnetic separation device and the sample was mixed by vortexing for 5 seconds and replaced. Finally the tube was left in the separator for an additional 10 minutes to affect separation. The rest of the procedure to process the sample was the same as that described above for sample 1. A third sample was treated identically to sample number 2, except it was removed from the separator, vortexed and returned every five minutes. A fourth sample was treated identically to sample number 2, except that it was only removed from the separator, vortexed and returned at the end of the 15 minute period and then left in magnetic separation device for 10 minutes to affect separation. These experiments were performed in duplicate and the results are shown in Table III and expressed as % recovery of added PC3 cells.

TABLE III

| Sample number | Incubation conditions | Recovery of PC3 cells (%) | Average PC3 cells recovery (%) |
|---|---|---|---|
| 1 | cells + anti-EpCAM-FF at R.T. for 15 min., no mixing | 20<br>20 | 20 |
| 2 | cells + anti-EpCAM-FF in magnetic separator, removed, vortexed 5 sec, returned each minute. 15 min total. | 37<br>28 | 32 |
| 3 | cells + anti-EpCAM-FF in magnetic separator, | 52<br>55 | 53 |

TABLE III-continued

| Sample number | Incubation conditions | Recovery of PC3 cells (%) | Average PC3 cells recovery (%) |
|---|---|---|---|
| 4 | removed, vortexed 5 sec, returned; every 5 min.. 15 min total. cells + anti-EpCAM-FF in magnetic separator, removed at 15 min, vortexed 5 sec, returned. 15 min total. | 41 48 | 44 |

The data show that there was a very significant increase in recovery of PC3 cells when blood and magnetic particles were incubated in the presence of a magnetic gradient that effectuates translation of the magnetic nanoparticles relative to cells. Various modifications of the incubation schemes in the presence of a magnetic gradient consistently resulted in a greater recovery of PC3 cells as compared to incubation schemes done in the absence of magnetic gradients. There were some differences in recovery of PC3 cells between different incubations in the magnetic device. Processes whereby ferrofluid is passed by target cells three times appears to give the best results.

Similar experiments demonstrate that recovery of target tumor cells is reduced when free EpCAM MAb was added to samples incubated at room temperatures prior to the magnetic separation step. When EpCAM-MAb is added prior to separation, in the absence of ferrofluid translation, separation efficiency is markedly decreased, particularly for relatively low determinant density cells, e.g., PC3. With high determinant density cells such as SKRB3, the effect is less dramatic. See Table IV.

TABLE IV

| Incubation conditions | Quench with excess EpCAM MAb before magnetic separation | PC3 cells Recovery (%) | Average (%) | SKBR3 cells Recovery (%) | Average (%) |
|---|---|---|---|---|---|
| Incubation @R.T. no FF translation | No | 28 34 | 31 | 71 70 | 70.5 |
| Incubation @R.T. no FF translation | Yes | 2.7 2.4 | 2.5 | 47 38 | 42 |
| Incubation with FF translation | No | 77 81 | 79 | 83 84 | 83.5 |
| Incubation with FF translation | Yes | 55 35 | 45 | 86 82 | 84 |

EXAMPLE 10

Increases in Cell Labeling can be Obtained with Cells Expressing a Large Range of Antigen Densities Cells from the bladder cancer line T24, the prostate cancer cell line PC3 and the breast cancer cell line SKBR-3 express varying densities of the EpCAM antigen on the cell surface. Antigen density was assessed by staining the cells with a fluoresceinated monoclonal antibody specific for EpCAM. As compared to the fluorescence intensity of the unstained cells, the mean fluorescence intensity of the T24 cells was 2 fold higher, the PC3 cells 8 fold higher and the SKBR3 cells 50 fold higher, as indicated in Table V below. To assess the effects of such a range of antigen densities on the principle underlying this invention, the following experiment was conducted. Aliquots of washed blood cells (1 ml) were added to 12×75 mm polystyrene tubes followed by 0.5 ml of dilution-wash buffer. Cell buffer (50 µl) containing a known number of tumor cells for each cell line was spiked into the respective samples. Anti-EpCAM-FF (20 µl) was added to each sample to final concentration of 5 µg/ml. The samples were mixed well and appropriate pairs were either incubated at room temperature without mixing for 15 minutes or placed in the magnetic separator for 15 minutes. As above, all samples were vortexed well and placed into magnetic separators for 10 minutes to effect separation.

The recovered cells were stained with appropriate labeled antibodies to determine the recovery of spiked tumor cells by flowcytometry as described above. The results shown in Table V below demonstrate that a significant increase in tumor cell recovery is achieved by performing the incubation under the influence of a magnetic gradient that induces ferrofluid translation relative to target analytes. It is noteworthy that the effect is more pronounced in the tumor cells having lower EpCAM density.

TABLE V

| Tumor cells | EpCAM density on tumor cells (Relative fluorescence intensity) | Regular incubation (incubation outside magnetic separator) | | Magnetic incubation (incubation inside magnetic separator) | |
|---|---|---|---|---|---|
| | | Recovery of cells (%) | Average recovery (%) | Recovery of cells (%) | Average recovery (%) |
| T24 (bladder) | 2 | 1.8 1.5 | 1.7 | 12 16 | 14 |
| PC3 (prostate) | 8 | 20 20 | 20 | 41 48 | 44 |
| SKBR3 (breast) | 53 | 71 70 | 71 | 83 84 | 84 |

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for enhancing binding interactions between members of a specific binding pair in a carrier medium, the first member being mobile throughout said carrier medium, and the second member being affixed to a magnetic particle, said particle also being mobile throughout said carrier medium, said method comprising performing a separation step immediately following introduction of one binding pair member into said carrier medium comprising the other binding pair member, said separation being caused by gravitational, electrical, or magnetic forces.

2. A method as claimed in claim 1, wherein said one member of said specific binding pair is initially caused to move in one direction and subsequently caused to move in a different direction.

3. A method as claimed in claim 1, wherein said specific binding pair member is selected from the group consisting of biotin-streptavidin, antigen-antibody, mimetope-antibody, receptor-hormone, receptor-ligand, agonist-antagonist, lectin-carbohydrate, Protein A-antibody Fc, and avidin-biotin.

4. A method as claimed in claim 1, wherein said one specific binding pair member is provided on the surface of a particulate magnetic material, said other specific binding pair member is a determinant of a target analyte, and said particulate magnetic material is caused to move through said medium under the influence of a magnetic field gradient.

5. A method as claimed in claim 1, wherein said one member of a specific binding pair comprises a target analyte and is selected from the group consisting of hormones, proteins, peptides, lectins, drugs, nucleic acid molecules, cells, viruses, and bacteria.

6. A method as claimed in claim 4, wherein said magnetic material has a particle size in the range of 50 nm to 50 μm.

7. A method as claimed in claim 6 wherein said magnetic material has a particle size in the range of 90–400 nm.

8. A method as claimed in claim 4, wherein said specific binding pair member on said magnetic particle is an anti-epithelial cell adhesion molecule (EpCAM) antibody; said target analyte is a tumor cell; and said determinant on said target analyte is EpCAM.

* * * * *